| United States Patent [19] | [11] Patent Number: 4,668,816 |
| Epstein | [45] Date of Patent: May 26, 1987 |

[54] HIGH YIELD CARBONYLATION OF HALO-HYDROCARBONS

[75] Inventor: Ronald A. Epstein, Yonkers, N.Y.

[73] Assignee: Stauffer Chemical Company, Westport, Conn.

[21] Appl. No.: 796,687

[22] Filed: Nov. 12, 1985

[51] Int. Cl.$^4$ .............................................. C07C 69/76
[52] U.S. Cl. .................................. 560/105; 562/406; 560/105; 560/232; 560/233; 560/206; 560/207
[58] Field of Search ............... 560/105, 232, 233, 206, 560/207; 562/406

[56] References Cited

U.S. PATENT DOCUMENTS 4,480,121 10/1984 Klun et al. ........................... 560/206

*Primary Examiner*—Paul J. Killos
*Attorney, Agent, or Firm*—Vivienne T. White

[57] ABSTRACT

High yields of aromatic, aromatic acetic and olefinic acids, esters, amides and the like are derived from a process wherein a halo-hydrocarbon is carbonylated in the presence of a palladium catalyst, a hindered amine base and phosphine in excess. The hindered amine base can comprise $C_3$-$C_{10}$ branched alkyls, cyclic compounds, or mixtures of the above. The preferred amine is N,N-diisopropylethyl amine. The preferred catalyst is $PdCl_2(PPH_3)_2$ with the excess phosphine generally supplied by a compound of the formula $PR^1R^2R^3$ where $R^1$, $R^2$ and $R^3$ are preferably phenyl.

17 Claims, No Drawings

HIGH YIELD CARBONYLATION OF HALO-HYDROCARBONS

BACKGROUND OF THE INVENTION

1. Field of the Invention

The invention is directed to the carbonylation of halo-hydrocarbons to produce aromatic, aromatic acetic and olefinic acids, esters, thioesters, amides, and the like.

2. Related Art

It is known to carbonylate halo-hydrocarbons such as benzyl chloride by reaction with carbon monoxide and an alcohol at 100° C. or below and at atmospheric pressures in the presence of an amine and a catalytic amount of a palladium catalyst to form esters.

An article entitled "Palladium-Catalyzed Carboalkoxylation of Aryl, Benzyl, and Vinylic Halides" by A. Schoenberg et al. appearing in The Journal of Organic Chemistry, Vol. 39, page 3318, (1974) discloses a process whereby aryl and vinylic bromides and iodides and benzyl chloride are each reacted with carbon monoxide and an alcohol at 100° C. or below and at atmospheric pressures in the presence of a tertiary amine and a catalytic amount of a palladiumtriphenylphosphine complex to form esters. The tertiary amines disclosed in tributyl amine. There is no teaching or disclosure relative to use of branched tertiary aliphatic amines or excess phosphine in the process.

U.S. Pat. No. 3,116,306 discloses a process for preparing carboxylated organic compounds by reacting (1) an organic compound represented by the general formula $R_nZ$ in which R is an organic compound having at least one aliphatic radical or cycloaliphatic radical, Z is $SO_4$, X, $X_2$ or $R'SO_3$, X being a halogen and R' is alkyl, alkenyl, cycloalkyl, aryl or aralkyl, where n is 1, Z is X, $X_2$ or $R'SO_3$, and when n is 2, Z is $SO_4$, the Z substituent being attached to an aliphatic or cycloaliphatic primary or secondary carbon atom; (2) carbon monoxide; (3) a salt of a metal hydrocarbonyl of the group consisting of cobalt hydrotetracarbonyl and iron dihydrotetracarbonyl and (4) a material of the group consisting of water, alcohols, phenols, mercaptans, ammonia, hydrazine, primary organo-nitrogen bases and secondary organo-nitrogen bases.

The above cited patent discloses that tertiary amines such as dicyclohexylethylamine have been found to be of general use in the process of the invention.

U.S. Pat. No. 3,708,529 teaches a process for synthesizing phenylacetic acid by carbonylation of benzyl chloride. The process discloses reacting benzyl chloride and carbon monoxide under atmospheric pressure at temperatures from 20° C. to 80° C. in a water-methanol medium containing up to 35% water, using a catalyst mixture consisting of a cobalt salt, an iron-manganese alloy and a sulfurated promoting agent.

There is no description of utilizing a hindered amine base in conjunction with a palladium catalyst in any of the above references or the use of an excess of phosphine in the process.

U.S. Pat. No. 4,480,121 discloses the palladium catalyzed carbonylation of 2-halo-1-alkenes, and the use of several amine compounds as bases which are within the description of the hindered amine base utilizing the instant invention.

In an article entitled "Carboalkoxylation of Aryl and Benzyl Halides Catalyzed by Dichlorobis(triphenylphosphine)palladium (II)" by John K. Stille et al. appearing in the Journal of Organic Chemistry, Vol. 40, pages 532 (1975) there is disclosed a process for the carbonylation of organic halides using palladium catalysts. The article mentions the severe reaction conditions required using palladium catalysts (200 psi and a reaction time of greater than or equal to 20 hrs.). Also mentioned is the use of tertiary amine bases in the process. The amine compounds mentioned in the article are triethylamine, 2,6 lutidine, and 1,8-bis(dimethylamino)-napthalene.

In a paper entitled "Carboxymethylation of Organic Halides by Palladium Complexes under Mild Conditions" by Masanobu Hidai et al. appearing in the Bulletin of the Chemical Society of Japan, Vol. 48 (7), pages 2075–2077 (1975) there is disclosed the carboxymethylation of various organic halides under what are described as very mild conditions. The article discloses that the carbonylation of organic halides by transition metal complexes have been reported but that the reactions required high temperatures and pressures with low yields of the carbonylated products. In the article there is described a process using palladium complexes and, as an amine source, diethyl amine. There is further described the use of other amines such as, for instance, dicyclohexyl amine. There is no disclosure or suggestion of using a tertiary amine or, more importantly, a hindered tertiary amine having, for example, branched alkyl groups thereon.

In none of the above references is there taught, suggested or shown the combination of a hindered tertiary amine base in combination with a palladium catalyst and an excess of phosphine.

SUMMARY OF THE INVENTION

A novel process whereby high yields of aromatic, aromatic acetic and olefinic acids, esters, thioesters, amides, and the like can be obtained under mild conditions by the carbonylation of a halo-hydrocarbon has been discovered. The process comprises carbonylating the halo-hydrocarbon in the presence of an alcohol, a soluble palladium catalyst and a tertiary hindered amine base wherein the catalyst is used in combination with an excess of phosphine. The hindered amine base can comprise an amine having branched alkyl constituents thereon ranging from $C_3$–$C_{10}$; cyclic compounds and aromatic compounds or mixtures of the above. A particularly suitable hindered amine compound is diisopropylethyl amine.

DETAILED DESCRIPTION OF THE INVENTION

The process comprises the carbonylation of a halohydrocarbon compound having the formula RX in the presence of an alcohol under relatively mild conditions to give high yields of aromatic, aromatic acetic and olefinic acids, esters, amides, thioesters, and the like using a soluble palladium catalyst combined with phosphine in excess in the presence of a hindered tertiary amine base. The invention comprises the use of a hindered amine base in conjunction with a soluble palladium catalyst combined with an excess of phosphine.

In general the hindered tertiary amine compound is one having at least two branched aliphatic or cycloaliphatic groups or one in which the N atom is in a cycloaliphatic or aromatic ring, substituted in a manner that induces steric crowding around the N atom. Primary and secondary amines can react with the carbonylated intermediate to form an amide. Generally such compounds comprise the formula $R'_3N$ wherein $R'$ can comprise a branched $C_3$-$C_{10}$ aliphatic constituent or combinations of branched aliphatic and straight chained aliphatic compounds having from 1-10 carbon atoms; a cyclic compound or an aromatic compound or combinations of the above.

An example of such a reaction is as follows:

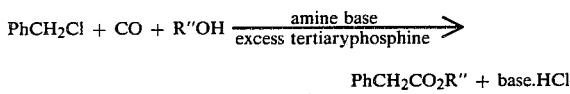

$$PhCH_2Cl + CO + R''OH \xrightarrow[\text{excess tertiaryphosphine}]{\text{amine base}}$$

$$PhCH_2CO_2R'' + base.HCl$$

wherein $R''$ is an alkyl of from $C_1$ to $C_{10}$, cycloalkyl, or aryl group. As used herein, the abbreviation "Ph" is meant to indicate a phenyl moiety.

For the purposes of this invention, the symbol R in the formula RX may be ethylenically unsaturated aliphatic radicals such as ethenyl, methallyl, butenyl, pentenyl, undecenyl, allyloxymethyl, methylallyloxymethyl, and the like; cycloaliphatic or aliphatic substituted or unsubstituted aralkyl radicals such as benzyl, phenethyl, phenylpropyl, phenylallyl, p-vinylbenzyl, phenylisopropyl, phenyloctyl, methoxybenzyl, xylyl, alpha-methylnaphthyl, beta-methylnaphthyl, and the like; and heterocyclic radicals such as methylene thiophene, dimethylene thiophene, and the like.

It has been found that organic halides suitable for the purposes of this invention are monohalogen and dihalogen, substituted or unsubstituted organic compounds having at least one aliphatic or cycloaliphatic radical within the molecule and in which the halogen is attached to primary or secondary carbon atoms within said aliphatic or cycloaliphatic radicals. By way of example, but not in limitation of the invention, suitable organic halides include alkenyl halides, such as allyl chloride, allyl bromide, methallyl chloride pentenyl chloride, pentenyl iodide, undecenyl chloride, dichloropentene, and the like; aralkyl halides, such as benzyl chloride, ortho-, meta- and paramethoxy benzyl chlorides, alpha-monochloro-xylene and alpha, alpha'-dichloro-xylene (ortho, meta or para), alpha-chloromethyl-naphthalene, beta-chloromethylnaphthalene, alpha-chloromesitylene, benzyl bromide, benzyl iodide, veratryl chloride, alpha-iodoxylene (ortho, meta or para), methyl p-chloromethylbenzoate, and the like; haloesters, such as methyl chloroacetate, ethyl bromoacetate, methyl 2-chloropropionate, and the like; salts of haloacids, such as sodium chloroacetate, sodium chloropropionate, and the like; and heterocyclic halides, such as chloromethylthiophene, and the like.

Catalysts for practicing the invention are derived from palladium (II) complexes exemplified by the general formula $PdX_2L_2$ where X=halide and L=tertiary phosphine or a group such as benzonitrile which will exchange with tertiary phosphine in solution or $PdX_4^{2-}$ or $PdCl_2$ which will react with tertiary phosphine to yield $PdX_2L_2$; or palladium (0) complexes exemplified by 1) $PdL_n$ where L=tertiary phosphine and n=2-4, or L=dibenzylidene acetone and n=2 (which will react with tertiary phosphine in solution), 2) $Pd_x(CO)_yL_z$ where L=tertiary phosphine, x=y=1 and z=3 or x=y=3, z=3 or 4. These complexes may be prepared in situ or prior to being added to the reaction.

It has been found that suitable catalysts include $PdCl_2(PPh_3)_2$, $PdCl_2(PhC\equiv N)_2$, and $PdCl_2(CH_3C\equiv N)_2$. The moiety $(PPh_3)$ is triphenyl phosphine.

An excess of phosphine is used in the process over that generally supplied in the formulae $PdX_2L_2$ or $Pd_x(CO)_yL_z$ which has a ratio of phosphine to palladium of 2:1. The molar ratio of L as where L is a tertiary phosphine to Pd used should be from over about 2:1 to about 100:1 and preferably from about 3:1 to about 30:1. Since the ratios given are molar ratios they would be the same if expressed as the ratio of P:Pd or $PPh_3$:Pd. Most desirably the molar ratio of phosphine to Pd should be 5:1 to 15:1. Suitable compounds for supplying excess phosphine include compounds of the formula $PR^1R^2R^3$ where $R^1,R^2$ and $R^3$ are phenyl, or substituted phenyl such as ortho, meta or para tolyl, methoxy phenyl or phenyl ethyl.

The amount of catalyst utilized in the process ranges from about 10 mole % of the halo-hydrocarbon to about 0.01 mole % and preferably from about 0.6 to about 0.02 mole %.

An excess of carbon monoxide over theoretical stoichiometric requirements is utilized in the process. Preferably a large excess of carbon monoxide is employed and the reaction is usually and conveniently carried out in an atmosphere of carbon monoxide. However, pure carbon monoxide need not necessarily be used in this reaction and mixtures of carbon monoxide with such gases as nitrogen, argon, methane, ethane, and the like, which are inert with respect to the carbonylation reaction, are entirely satisfactory for the purposes of this invention.

A wide range of pressure has been found suitable for the purposes of this invention, from about atmospheric or less to about 351.54 Kg/sq.cm (5,000 lbs/in²) or more. Pressures between about atmospheric and about 35.15 Kg. sq.cm (500 lbs/in²) is desirable while from atmospheric to 100 lbs/in² (7.03 Kg/cm²) is preferred. Similarly, the process of this invention can be carried out within a wide range of temperatures, from about 0° C. to about 150° C. or even higher. Preferred temperatures are from about 40° C. to about 100° C. The formation of some esters are more rapid as compared to other esters. As such the preferred process temperature necessary for preparing the various esters may vary considerably.

A hydrogen halide acceptor is used to make the carbonylation process catalytic. In its absence free hydrogen halide is not formed. An amine is added to the reaction to function as a hydrogen halide acceptor. When an amine is used as a hydrogen halide acceptor, an amine hydrogen halide salt is formed. Suitable amines are represented by any hindered amine base such as, for instance, diisopropylethyl amine, diisopropyl methyl amine and dicyclohexyl ethyl amine are suitable for use in the practice of the invention. At least one mole of amine for each mole of hydrogen halide produced should be added to the reaction.

Typical alcohols suitable for the purposes of this invention include aliphatic alcohols such as methyl alcohol, ethyl alcohol, propyl alcohol, isopropyl alcohol, n-butyl alcohol, secondary butyl alcohol, n-hexyl alcohol, hexanol-2, n-octyl alcohol, capryl alcohol, isopropyl dodecyl alcohol, stearyl alcohol, ceryl alcohol, myricyl alcohol, and the like; polyhydric compounds such as ethylene glycol, diethylene glycol, glycerol, pentaerythritol, and the like; olefinic alcohols such as allyl alcohol, crotyl alcohol, buten-1-ol-4, penten-1-ol-5, 2,6-dimethylocten-1-ol-8, 3,7,11,15-tetramethylhexadecen-2-ol-1, and the like; cycloaliphatic alcohols such as cyclopentyl alcohol, cyclohexyl alcohol, methyl cyclohexyl alcohol, and the like; aralkyl alcohols such as benzyl alcohol, diphenylcarbinol, phenylethyl alcohol, phenyl propyl alcohol, cinnamyl alcohol, and the like.

Although the instant invention can be practiced in the presence of water, practicing the invention under anhydrous conditions is also desirable.

It will be apparent from the foregoing description, therefore, that the present invention provides a new and useful process for the preparation of all manner of carboxylated organic compounds. Furthermore, the carboxylated organic compounds produced thereby are suitable for the various conventional uses for such products, such for example, as solvents, as plasticizers for synthetic and natural polymeric materials, as surface active agents, as in the manufacture of insecticides, miticides and fungicides, as ingredients in the manufacture of synthetic resins and polymers, and the like.

The following Examples are descriptive of the process of the invention.

EXAMPLE 1

Into a 12 oz. (350 ml) glass reactor equipped with a gas inlet and outlet, thermocouple, and magnetic stir bar was placed 0.201 g $PdCl_2(PPh_3)_2$ (0.286 mmole) and 0.592 g $PPh_3$ (2.26 mmole). The reactor was sealed, evacuated, and filled with $N_2$. Under a $N_2$ purge, deoxygenated benzyl chloride, 7.97 g (63.0 mmole), isopropanol, 74.0 g (1.23 mole) and N,N diisopropylethyl amine, 14.2 g (110 mmole) were added. The $PPh_3$ to Pd ratio was 10:1.

The reactor was flushed with high purity CO, presurized to 30 psig and heated to 100° C. The reactor was then maintained at 45 psig (3.16 Kg/sq.cm) by feeding CO to the reactor on demand. After 2 hr at 100° C., the reactor was cooled and vented. Gas Chromatographic analysis (GC) of the reaction product revealed a 100% conversion of benzyl chloride with a 97% yield of isopropyl phenylacetate and 2% benzyl isopropyl ether.

EXAMPLE 2

The carbonylation was performed in methanol in equipment similar to that used in Example 1, except that the reactor was equipped with a mechanical stirrer. 0.200 g $PdCl_2(PPh_3)_2$ (0.286 mmole), 0.150 g $PPh_3$ (0.572 mmole), 7.71 g benzyl chloride (60.8 mmole), 70 g deoxygenated methanol (2.18 mole), and 11.20 g diisopropylethyl amine (86.7 mmole), were used. The reactor was heated under 15 psig of CO. At 78° C. CO uptake was noticed and the reactor brought to 45 psig (3.16 Kg/sq.cm) with CO. Uptake continued for about 1 hr. during which time the reactor heated to about 85° C. GC analysis showed a nearly quantitative conversion of the benzyl chloride to methyl phenylacetate. The ratio of $PPh_3$ to Pd was 4:1.

EXAMPLE 3

15.2 g benzyl chloride (0.120 mole), 20.6 g of diisopropylethyl amine (0.159 mole), 75 ml methanol, 0.05 g $PdCl_2(PPh_3)_2$ (0.071 mmole), and 0.114 g $PPh_3$ (0.43 mole) are placed into a reactor as described in Example 3. After reaction at 80° C., 43 psig (3.0 Kg/sq.cm) CO for 100 min., a 99% conversion with a 99% selectivity to methyl phenylacetate was obtained. The ratio of $PPh_3$ to Pd was 8:1.

COMPARATIVE EXAMPLE 1

Using the same reactor and procedure as in Example 1, 7.50 g benzyl chloride (59.2 mmole), 20.95 g tributylamine (113.0 mmole) and 77 g isopropanol (1.28 mole) were reacted at 100° C., 45 psig (3.16 Kg/sq.cm) in the presence of 0.202 g $PdCl_2$ (0.288 mmole) and 0.591 g $PPh_3$ (0.225 mmole). After 3½ hrs the reactor was cooled, and an additional 2 g of benzyl chloride (15.8 mmole) was added, and the reactor reheated to 100° C. for an additional 1 hr 50 min. The reactor was then cooled and vented. GC analysis revealed that all of the benzyl chloride had reacted with a 47% selectivity to the isopropyl ester and 1% to the ether. The $PPh_3$ to Pd ratio was 9.8:1.

COMPARATIVE EXAMPLE 2

As in Example 1, 6.50 g benzyl chloride (51.3 mmole), 27.91 g trioctylamine (79 mmole), and 67.9 g isopropanol (1.13 mole) were reacted at 100° C., 45 psig (3.16 Kg/sq.cm) for 5 hrs using 0.202 g $PdCl_2(PPh_3)_2$ (0.288 mmole) and 0.659 g $PPh_3$ (2.51 mmole) as the catalyst system. GC analysis revealed a 99% conversion of the benzyl chloride with a 30% selectivity to isopropyl phenyl acetate and 2% to benzyl isopropylether.

COMPARATIVE EXAMPLE 3

Using the same reactor and procedure as in Example 3, 7.44 g benzyl chloride (59.8 mmole) is carbonylated in 62 g methanol (1.97 mole) with 9.8 g diisopropyl ethyl amine (75.8 mmole), and 0.2047 g bis(triphenylphosphine)iminium tetracarbonyl cobaltate (0.289 mmole) as catalyst. The reaction is run at 80° C. 45 psig (3.16 Kg/sq.cm) CO for 4 hrs. A 79% conversion of the benzyl chloride with an 83% selectivity to methyl phenylacetate was obtained.

COMPARATIVE EXAMPLE 4

The same procedure as in Example 1 was used with 52.1 mg $PdCl_2(PPh_3)_2$ (0.074 mmole), 1.65 g benzyl chloride (13.0 mmole), 20.8 g isopropanol (0.346 mole) and 2.60 g N,N diisopropylethylamine (20.1 mmole). GC analysis after 4.5 hr at 100° C. revealed a 95% conversion of the benzyl chloride with a 89% selectivity to isopropylphenyl acetate and 4% benzyl isopropyl ether. In comparison to Example 1, where a $PPh_3$:Pd ratio of 10:1 was used, this Example shows that a lower ratio of 2:1.

What is claimed is:

1. A process for carbonylating halo-hydrocarbons comprising carbonylating the halo-hydrocarbon in the presence of an alcohol, CO, a hindered amine base in conjunction with a palladium catalyst and an excess of phosphine.

2. The process of claim 1 wherein the hindered amine has the formula $R'_3N$ wherein R' comprises $C_3-C_{10}$ branched aliphatic radicals, straight chained aliphatic radicals having 1–10 carbon atoms, cyclic radicals and aromatic radicals or mixtures of the above and wherein $R'_3N$ comprises not more than one straight chained aliphatic radical.

3. The process of claim 2 wherein the tertiary hindered amine is N,N-diisopropylethyl amine.

4. The process of claim 2 wherein the tertiary hindered amine is N,N-diisopropylmethyl amine.

5. The process of claim 2 wherein the tertiary hindered amine is dicyclohexyl ethyl amine.

6. The process of claim 1 wherein the excess phosphine is added in the form of triphenyl phosphine.

7. The process of claim 1 wherein the palladium catalyst is palladium II complexes having the formula $PdX_2L_2$ wherein X is a halide and L is a tertiary phosphine.

8. The process of claim 7 wherein the palladium catalyst is $PdCl_2(PPh_3)_2$.

9. The process of claim 1 wherein the palladium catalyst is a palladium 11 complex having the formula $PdX_2L_2$ wherein X is a halide and L is benzonitrile.

10. The process of claim 1 wherein the aromatic halide is benzyl chloride.

11. The process of claim 9 wherein the benzonitrile reacts with phosphine in situ.

12. The process of claim 1 wherein the alcohol is isopropanol.

13. The process of claim 1 wherein the alcohol is methanol.

14. The process of claim 1 conducted under anhydrous conditions.

15. The process of claim 1 wherein the phosphine to palladium ratio is above about 2:1 to 100:1.

16. The process of claim 15 wherein the phosphine to palladium ratio is from about 3:1 to 30:1.

17. The process of claim 16 wherein the phosphine to palladium ratio is from about 5:1 to 15:1.

* * * * *

UNITED STATES PATENT AND TRADEMARK OFFICE
CERTIFICATE OF CORRECTION

PATENT NO.  : 4,668,816
DATED       : May 26, 1987
INVENTOR(S) : Ronald A. Epstein It is certified that error appears in the above-identified patent and that said Letters Patent is hereby corrected as shown below:

Abstract, Front Page, 9th line, "$(PPH_3)_2$" should be --$(PPh_3)_2$--;

Col. 1, line 25, "palladiumtriphenylphosphine" should be --palladium triphenylphosphine--;

Col. 1, line 26, "in" should be --is--;

Col. 2, line 2, "pages" should be --page--;

Col. 3, line 11, "tertiaryphosphine" should be --tertiary phosphine--;

Col. 3, line 25, "methoxybenzyl" should be --methoxylbenzyl--;

Col. 6, line 8, "(0.225 mmole)" should be --(2.25 mole)--;

Col. 7, line 12, "11" should be --II--.

Signed and Sealed this

Twenty-ninth Day of August, 1989

Attest:

DONALD J. QUIGG

Attesting Officer

Commissioner of Patents and Trademarks